United States Patent
Won et al.

(10) Patent No.: US 10,619,198 B2
(45) Date of Patent: *Apr. 14, 2020

(54) PCR PRIMER LINKED TO COMPLEMENTARY NUCLEOTIDE SEQUENCE OR COMPLEMENTARY NUCLEOTIDE SEQUENCE INCLUDING MIS-MATCHED NUCLEOTIDES AND METHOD FOR AMPLIFYING NUCLEIC ACID USING THE SAME

(71) Applicant: SD BIOSENSOR, Suwon-si (KR)

(72) Inventors: Yoo-Deok Won, Yongin-si (KR); Hae-joon Park, Yongin-si (KR); Sunyoung Lee, Yongin-sl (KR)

(73) Assignee: SD BIOSENSOR, Inc., Suwon-si (KR)

( * ) Notice: Subject to any disclaimer, the term of this patent is extended or adjusted under 35 U.S.C. 154(b) by 61 days.

This patent is subject to a terminal disclaimer.

(21) Appl. No.: 15/545,996

(22) PCT Filed: Jan. 7, 2016

(86) PCT No.: PCT/KR2016/000151
§ 371 (c)(1),
(2) Date: Jul. 24, 2017

(87) PCT Pub. No.: WO2016/122135
PCT Pub. Date: Aug. 4, 2016

(65) Prior Publication Data
US 2018/0002746 A1 Jan. 4, 2018

(30) Foreign Application Priority Data
Jan. 30, 2015 (KR) .................. 10-2015-0015276

(51) Int. Cl.
*C12Q 1/6853* (2018.01)
*C12Q 1/68* (2018.01)
*C12Q 1/686* (2018.01)

(52) U.S. Cl.
CPC ............ *C12Q 1/6853* (2013.01); *C12Q 1/68* (2013.01); *C12Q 1/686* (2013.01)

(58) Field of Classification Search
None
See application file for complete search history.

(56) References Cited

U.S. PATENT DOCUMENTS 5,283,175 A * 2/1994 Weaver .................. C12Q 1/689
435/6.16
6,365,729 B1 4/2002 Tyagi et al.
(Continued)

FOREIGN PATENT DOCUMENTS

JP 2008531040 8/2008
JP 2009005592 1/2009
(Continued)

OTHER PUBLICATIONS

Takei et al. Chemical Communication 2014; 50: 15195. (Year: 2014).*

(Continued)

*Primary Examiner* — Angela M. Bertagna

(57) ABSTRACT

The present invention relates to a primer for PCR obtained by, directly or through inosine as a linker, linking a complementary nucleotide sequence or a complementary nucleotide sequence including a mis-matched nucleotide sequence to the 5'-terminal of a forward or reverse primer; and to a PCR method including a step of mixing a nucleic acid template in a PCR composition including the primer and then performing PCR on the mixture. The primer for PCR of the present invention includes a complementary nucleotide sequence or a mis-matched nucleotide sequence in a complementary nucleotide sequence, which is linked to the 5'-terminal thereof directly or via a linker, thereby lowering the sensi- (Continued)

tivity increase due to the increase in amplification products and reducing non-specifically occurring reactions in PCR.

2 Claims, 15 Drawing Sheets

Specification includes a Sequence Listing.

(56) References Cited

U.S. PATENT DOCUMENTS

| | | | |
|---|---|---|---|
| 2003/0045488 A1* | 3/2003 | Brown | C12N 15/113 514/44 A |
| 2003/0175749 A1 | 9/2003 | Chun | |
| 2009/0258353 A1 | 10/2009 | Yoon et al. | |
| 2011/0269192 A1 | 11/2011 | Ruan et al. | |
| 2014/0274810 A1* | 9/2014 | Arnold | C12N 15/1065 506/26 |
| 2016/0068903 A1* | 3/2016 | Zhou | C12Q 1/686 536/24.33 |

FOREIGN PATENT DOCUMENTS

| | | |
|---|---|---|
| JP | 2013518559 | 5/2013 |
| KR | 1009771860000 | 8/2010 |

OTHER PUBLICATIONS

Jong-Yoon Chun et al., "Dual priming oligonucleotide system for the multiplex detection of respiratory viruses and SNP genotyping of CYP2C19 gene," Nucleic Acid Research, 2007, vol. 35, No. 6.

Fumie Takei et al, "Detection of hepatitis C virus by single-step hairpin primer RT-PCR", Bioorganic & Medical Chemistry Letters, vol. 24, No. 1, Jan. 1, 2014 (Jan. 1, 2014), pp. 394-396.

M.H. Hazbon et al, "Hairpin Primers for Simplified Single-Nucleotide Polymorphism Analysis of *Mycobacterium tuberculosis* and Other Organisms", Journal of Clinical Microbiology, vol. 42, No. 3, Mar. 2004 (Mar. 1, 2004), pp. 1236-1242.

* cited by examiner

SEQUENCE LISTING

<160> NUMBER OF SEQ ID NOS: 29

<210> SEQ ID NO 1
<211> LENGTH: 25
<212> TYPE: DNA
<213> ORGANISM: Artificial Sequence
<220> FEATURE:
<223> OTHER INFORMATION: TatF

<400> SEQUENCE: 1
gaattgggtg tcaacatagc agaat                                  25

<210> SEQ ID NO 2
<211> LENGTH: 27
<212> TYPE: DNA
<213> ORGANISM: Artificial Sequence
<220> FEATURE:
<223> OTHER INFORMATION: TatR

<400> SEQUENCE: 2
aatactatgg tccacacaac tattgct                                27

<210> SEQ ID NO 3
<211> LENGTH: 50
<212> TYPE: DNA
<213> ORGANISM: Artificial Sequence
<220> FEATURE:
<223> OTHER INFORMATION: Tat55 F-Ix0

<400> SEQUENCE: 3
attctgctta caactgaccc aattcgaatt gggtgtcaac atagcagaat        50

<210> SEQ ID NO 4
<211> LENGTH: 51
<212> TYPE: DNA
<213> ORGANISM: Artificial Sequence
<220> FEATURE:
<223> OTHER INFORMATION: Tat55 F-Ix1
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 4
attctgctta caactgaccc aattcngaat tgggtgtcaa catagcagaa t      51

<210> SEQ ID NO 5
<211> LENGTH: 51
<212> TYPE: DNA
<213> ORGANISM: Artificial Sequence
<220> FEATURE:
<223> OTHER INFORMATION: Tat55 F-Ix1_5
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 5
attcacgata cttgacaccc aattcngaat tgggtgtcaa catagcagaa t      51

```
<210> SEQ ID NO 6
<211> LENGTH: 51
<212> TYPE: DNA
<213> ORGANISM: Artificial Sequence
<220> FEATURE:
<223> OTHER INFORMATION: Tat55 F-Ix1_3
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 6
attctgctta caactgaccc aattcngaat tgggtgtcaa catagcagaa t            51

<210> SEQ ID NO 7
<211> LENGTH: 53
<212> TYPE: DNA
<213> ORGANISM: Artificial Sequence
<220> FEATURE:
<223> OTHER INFORMATION: Tat55 F-Ix3
<220> FEATURE:
<221> NAME/KEY: modified_base
<222> LOCATION: (26)..(28)
<220> FEATURE:
<221> NAME/KEY: misc_feature
<222> LOCATION: (26)..(28)
<223> OTHER INFORMATION: n is a, c, g, or t

<400> SEQUENCE: 7
attctgctta caactgaccc aattcnnnga attgggtgtc aacatagcag aat          53

<210> SEQ ID NO 8
<211> LENGTH: 55
<212> TYPE: DNA
<213> ORGANISM: Artificial Sequence
<220> FEATURE:
<223> OTHER INFORMATION: Tat55 F-Ix5
<220> FEATURE:
<221> NAME/KEY: modified_base
<222> LOCATION: (26)..(30)
<220> FEATURE:
<221> NAME/KEY: misc_feature
<222> LOCATION: (26)..(30)
<223> OTHER INFORMATION: n is a, c, g, or t

<400> SEQUENCE: 8
attctgctta caactgaccc aattcnnnnn gaattgggtg tcaacatagc agaat        55

<210> SEQ ID NO 9
<211> LENGTH: 57
<212> TYPE: DNA
<213> ORGANISM: Artificial Sequence
<220> FEATURE:
<223> OTHER INFORMATION: Tat55 F-Ix7
<220> FEATURE:
<221> NAME/KEY: modified_base
<222> LOCATION: (26)..(32)
<220> FEATURE:
<221> NAME/KEY: misc_feature
<222> LOCATION: (26)..(32)
<223> OTHER INFORMATION: n is a, c, g, or t

<400> SEQUENCE: 9
attctgctta caactgaccc aattcnnnnn nngaattggg tgtcaacata gcagaat      57

<210> SEQ ID NO 10
<211> LENGTH: 59
<212> TYPE: DNA
<213> ORGANISM: Artificial Sequence
<220> FEATURE:
<223> OTHER INFORMATION: Tat55 F-Ix9
```

```
<220> FEATURE:
<221> NAME/KEY: modified_base
<222> LOCATION: (26)..(34)
<220> FEATURE:
<221> NAME/KEY: misc_feature
<222> LOCATION: (26)..(34)
<223> OTHER INFORMATION: n is a, c, g, or t

<400> SEQUENCE: 10
attctgctta caactgaccc aattcnnnnn nnnngaattg ggtgtcaaca tagcagaat      59

<210> SEQ ID NO 11
<211> LENGTH: 51
<212> TYPE: DNA
<213> ORGANISM: Artificial Sequence
<220> FEATURE:
<223> OTHER INFORMATION: Tat F-Ix1
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 11
attctgctat gttgacaccc aattcngaat tgggtgtcaa catagcagaa t      51

<210> SEQ ID NO 12
<211> LENGTH: 51
<212> TYPE: DNA
<213> ORGANISM: Artificial Sequence
<220> FEATURE:
<223> OTHER INFORMATION: Tat65 F-Ix1
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 12
attctgctat caagacaccc aattcngaat tgggtgtcaa catagcagaa t      51

<210> SEQ ID NO 13
<211> LENGTH: 51
<212> TYPE: DNA
<213> ORGANISM: Artificial Sequence
<220> FEATURE:
<223> OTHER INFORMATION: Tat45 F-Ix1
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 13
attctggata caactgtgcc aattcngaat tgggtgtcaa catagcagaa t      51

<210> SEQ ID NO 14
<211> LENGTH: 51
<212> TYPE: DNA
<213> ORGANISM: Artificial Sequence
<220> FEATURE:
<223> OTHER INFORMATION: Tat45 F-Ix1_53
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t
```

<400> SEQUENCE: 14
attcacgtat gttgactggc aattcngaat tgggtgtcaa catagcagaa t    51

<210> SEQ ID NO 15
<211> LENGTH: 51
<212> TYPE: DNA
<213> ORGANISM: Artificial Sequence
<220> FEATURE:
<223> OTHER INFORMATION: Tat45 F-Ix1_53-4
<220> FEATURE:
<221> NAME/KEY: modified_base
<222> LOCATION: (26)..(26)
<220> FEATURE:
<221> NAME/KEY: misc_feature
<222> LOCATION: (26)..(26)
<223> OTHER INFORMATION: n is a, c, g, or t

<400> SEQUENCE: 15
attctgctta caactgtggc aattcngaat tgggtgtcaa catagcagaa t    51

<210> SEQ ID NO 16
<211> LENGTH: 20
<212> TYPE: DNA
<213> ORGANISM: Artificial Sequence
<220> FEATURE:
<223> OTHER INFORMATION: Beta-actin_F

<400> SEQUENCE: 16
agagatggcc acggctgctt    20

<210> SEQ ID NO 17
<211> LENGTH: 20
<212> TYPE: DNA
<213> ORGANISM: Artificial Sequence
<220> FEATURE:
<223> OTHER INFORMATION: Beta-actin_R

<400> SEQUENCE: 17
atttgcggtg gacgatggag    20

<210> SEQ ID NO 18
<211> LENGTH: 41
<212> TYPE: DNA
<213> ORGANISM: Artificial Sequence
<220> FEATURE:
<223> OTHER INFORMATION: B-actin65 F-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 18
aagcagccca ccccatctct nagagatggc cacggctgct t    41

<210> SEQ ID NO 19
<211> LENGTH: 41
<212> TYPE: DNA
<213> ORGANISM: Artificial Sequence
<220> FEATURE:
<223> OTHER INFORMATION: B-actin65 R-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 19
ctccatcgtg gtgcgcaaat natttgcggt ggacgatgga g          41

<210> SEQ ID NO 20
<211> LENGTH: 20
<212> TYPE: DNA
<213> ORGANISM: Artificial Sequence
<220> FEATURE:
<223> OTHER INFORMATION: GAPD N_F

<400> SEQUENCE: 20
accacagtcc atgccatcac          20

<210> SEQ ID NO 21
<211> LENGTH: 21
<212> TYPE: DNA
<213> ORGANISM: Artificial Sequence
<220> FEATURE:
<223> OTHER INFORMATION: GAPD N_R

<400> SEQUENCE: 21
tcccaccacc ctgttgctgt a          21

<210> SEQ ID NO 22
<211> LENGTH: 41
<212> TYPE: DNA
<213> ORGANISM: Artificial Sequence
<220> FEATURE:
<223> OTHER INFORMATION: GAPD55 F-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 22
gtgatgggta cctctgtggt naccacagtc catgccatca c          41

<210> SEQ ID NO 23
<211> LENGTH: 43
<212> TYPE: DNA
<213> ORGANISM: Artificial Sequence
<220> FEATURE:
<223> OTHER INFORMATION: GAPD55 R-Ix1
<220> FEATURE:
<221> NAME/KEY: modified_base
<222> LOCATION: (22)..(22)
<220> FEATURE:
<221> NAME/KEY: misc_feature
<222> LOCATION: (22)..(22)
<223> OTHER INFORMATION: n is a, c, g, or t

<400> SEQUENCE: 23
tacagcatgt cccacgtggg antcccacca ccctgttgct gta          43

<210> SEQ ID NO 24
<211> LENGTH: 41
<212> TYPE: DNA
<213> ORGANISM: Artificial Sequence
<220> FEATURE:
<223> OTHER INFORMATION: GAPD45 F-Ix1-2
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t -continued

<400> SEQUENCE: 24
gtgatgcgta cctgactggt naccacagtc catgccatca c         41

<210> SEQ ID NO 25
<211> LENGTH: 43
<212> TYPE: DNA
<213> ORGANISM: Artificial Sequence
<220> FEATURE:
<223> OTHER INFORMATION: GAPD45 R-Ix1-2
<220> FEATURE:
<221> NAME/KEY: modified_base
<222> LOCATION: (22)..(22)
<220> FEATURE:
<221> NAME/KEY: misc_feature
<222> LOCATION: (22)..(22)
<223> OTHER INFORMATION: n is a, c, g, or t

<400> SEQUENCE: 25
tacagcttgt cccacctggg antcccacca ccctgttgct gta         43

<210> SEQ ID NO 26
<211> LENGTH: 41
<212> TYPE: DNA
<213> ORGANISM: Artificial Sequence
<220> FEATURE:
<223> OTHER INFORMATION: B-actin55 F-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 26
aagcagcgca ccgcatctct nagagatggc cacggctgct t         41

<210> SEQ ID NO 27
<211> LENGTH: 41
<212> TYPE: DNA
<213> ORGANISM: Artificial Sequence
<220> FEATURE:
<223> OTHER INFORMATION: B-actin55 R-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 27
ctccatccag ctgcgcaaat natttgcggt ggacgatgga g         41

<210> SEQ ID NO 28
<211> LENGTH: 41
<212> TYPE: DNA
<213> ORGANISM: Artificial Sequence
<220> FEATURE:
<223> OTHER INFORMATION: B-actin45 F-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 28

```
aagcacggca ccggatctct nagagatggc cacggctgct t                              41
```

```
<210> SEQ ID NO 29
<211> LENGTH: 41
<212> TYPE: DNA
<213> ORGANISM: Artificial Sequence
<220> FEATURE:
<223> OTHER INFORMATION: B-actin45 R-Ix1
<220> FEATURE:
<221> NAME/KEY: modified_base
<222> LOCATION: (21)..(21)
<220> FEATURE:
<221> NAME/KEY: misc_feature
<222> LOCATION: (21)..(21)
<223> OTHER INFORMATION: n is a, c, g, or t

<400> SEQUENCE: 29
ctccatgtag ctgggcaaat natttgcggt ggacgatgga g                              41
```

PCR PRIMER LINKED TO COMPLEMENTARY NUCLEOTIDE SEQUENCE OR COMPLEMENTARY NUCLEOTIDE SEQUENCE INCLUDING MIS-MATCHED NUCLEOTIDES AND METHOD FOR AMPLIFYING NUCLEIC ACID USING THE SAME

TECHNICAL FIELD

The present invention relates to a primer for a nucleic acid polymerase chain reaction (hereinafter, referred to as "PCR"), in which the primer includes a complementary nucleotide sequence or a complementary nucleotide sequence including a mis-matched nucleotide sequence linked to 5' position of a primer directly or through a linker and a use thereof, and more specifically to a primer for PCR obtained by, directly or through inosine as a linker, linking a complementary nucleotide sequence or a complementary nucleotide sequence including a mis-matched nucleotide sequence to 5'-terminal of a forward or reverse primer, a PCR method including a step of mixing a nucleic acid template in a PCR composition including the primer and then performing PCR on the mixture, a complementary primer (CP), and a use thereof.

BACKGROUND ART

DNA polymerase, primer pair, dNTP, Mg++, and other buffers are required for PCR components which are essential for molecular diagnostic test or nucleic acid diagnostic test. The amplification of the interested target gene having high specificity and accuracy is required to use such a reaction widely.

Robust PCR performance requires highly sensitive analytical PCR such as single-copy DNA molecule detection (Wabuyele, M. B et al. Single Mol., 2001, 2: 13-21), bloodborne infection (Elnifro, E. M. et al. Clin. Microbiol. Rev., 2000, 13: 559-570), or the like.

Generally, in order to carry out PCR, the information about the target gene to be detected is obtained, and primer & probe design is performed. At this time, off-target amplification often occurs although the primer sequence and length designed are designed to well hybridize only to template DNA/RNA at annealing temperatures. It is considered that the reason for this is because of low-temperature conditions during PCR master-mix preparation and thermal cycler ramping to the initial denaturation temperature (Chou, Q et al. Nucleic Acids Res., 1992, 20: 1717-1723). Under such a condition, the primers are present at a higher concentration than the target, and the primers react non-specifically with partially complementary sites, or the primers react with each other. These non-specific primer complexes competitively react to the desired target site reaction, thereby impairing sensitivity to serve as a cause of high background. In particular, primer dimers may form complex mixtures with primer artifacts during PCR.

Several methods are widely used for increasing the specificity of PCR, and one method among them employs a hot start technique. This technique increases the temperature to maintain the specificity of the primer/target hybridization reaction so that the DNA polymerase interferes with the premature extension when preparing the pre-PCR mixture (Alexandre V. L et al., Lebedev A. V. et al., Nucleic Acids Res., 2008, 36: e131.). Other methods are used in which the reaction components are physically separated so as not to cause a PCR reaction (Quin chou et al., Nucleic Acids Res., 1992, 20: 1717-1723), accessary proteins are used (Clark, D. R. et al. US Pat. No. 2006057617), an antibody against a DNA polymerase is used, and a Mg++-pyrophosphate complex is formed to prevent a non-specific reaction at a low temperature (Bioneer).

In addition to increasing the specificity by controlling the reaction components, several methods have been reported to modify the primer to increase the specificity. Among them, there are a method of using to include competitor sequence, a method of using a secondary structure of a primer, a method of increasing a hybridization selectivity, and a dual priming oligo method using two types of primers to be attached to each other (for example, Seegene). Further, as a 3'-modification method, a method of blocking primer extension until the 3'→5' exonuclease has been removed, a method of blocking it by removal through UV irradiation, and a thermal deprotection method have been reported.

These methods have the effect of reducing the non-specific reaction, but they have disadvantages of using additional enzymes, adding extra activation conditions, specific nucleoside modification, difficulty in coverage for variants of the corresponding target gene due to structurally complex primer design, and a decrease of sensitivity.

PRIOR PATENT DOCUMENT

Korean Patent Publication No. 10-2004-0005426

DISCLOSURE

Technical Problem

The present invention has been made to overcome the above-mentioned problems and in view of the above-mentioned need, and an object of the present invention is to provide a primer which reduces the increased sensitivity and non-specific reaction due to an increase of amplification products in PCR.

Another object of the present invention is to provide a method for reducing the increased sensitivity and non-specific reaction due to an increase of amplification products in PCR.

Technical Solution

To achieve the objects, the present invention provides a primer for gene amplification as the following Structural Formula 1, in which the primer includes complementary double strands of nucleotides with a bubble structure by including a mis-matched nucleotide linked, directly or by an inosine linker, to 5' terminal of a primer for a corresponding sequence for amplifying a specific gene sequence:

[Structural Formula 1]

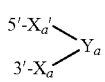

The primer includes a complementary nucleotide sequence $X_a$ of the corresponding sequence for amplifying the specific gene sequence and a mis-matched nucleotide sequence $X'_a$ which is complementary to $X_a$, in which $X_a$ and $X'_a$ are linked with a nucleotide sequence $Y_a$ of a universal base or a non-discriminatory base.

In one embodiment of the present invention, the primer is preferably a primer in which the bubble structure of the mis-matched nucleotide is linked with at least one double-strand sequence, and the primer is more preferably a primer in which the bubble structure of the mis-matched nucleotide is linked with one to four double-strand sequences, but is not limited thereto.

In another embodiment of the present invention, a primer preferably has a structure in which at least one bubble is included in the double-strand of $X'_a$ and $X_a$ of the primer, and more preferably has a structure in which one to three bubbles are included in the double-strand of $X'_a$ and $X_a$ of the primer, but is not limited thereto.

In another embodiment of the present invention, the primer is preferably a primer in which the number of mis-matched nucleotides in the complementary nucleotide sequence ($X'_a$) includes at least one nucleotide sequence, and the primer is more preferably a primer in which the number of mis-matched nucleotides in the complementary nucleotide sequence ($X'_a$) includes 3 to 12 nucleotide sequences, but is not limited thereto.

In still another embodiment of the present invention, the primer is preferably a primer having a bubble structure including at least 0 universal base or non-discriminatory base in $Y_a$, and the primer is preferably a primer having a bubble structure including 0 to 9 universal bases or non-discriminatory bases in $Y_a$, but is not limited thereto.

In one embodiment of the present invention, the primer is preferably, but not limited to, one or more primers selected from the group consisting of the primers as set forth in SEQ ID NOS: 3 to 15, SEQ ID NOS: 18 and 19, and SEQ ID NOS: 22 to 29.

In another embodiment of the present invention, the primer is used in each of forward and reverse positions for gene amplification or used in both.

The present invention also provides a method of amplifying a specific gene sequence from RNA, in which cDNA is synthesized with a reverse transcription polymerase for reverse transcription using the primer of the present invention, and the specific gene is amplified with the cDNA as a template using the primer of the present invention.

In one embodiment of the present invention, the method is such that the specific gene amplification reaction after performing the reverse transcription of an RNA template using the primer of the present invention is preferably carried out in an one-step process.

Further, the present invention provides a composition for amplifying a gene, which is used in a polymerase chain reaction method, a real-time polymerase chain reaction method, or an isothermal amplification method for gene amplification of DNA and RNA, which includes the primer of the present invention as an active ingredient.

In one embodiment of the present invention, the composition preferably further includes one or more polymerases selected from the group consisting of Taq polymerase having 5'→3' exonuclease activity, HotStart Taq polymerase, PFU polymerase, and Klenow polymerase having 5'→3' exonuclease (−) and 3'→5' exonuclease (−) activity, but is not limited thereto.

Further, the present invention provides a kit for amplifying a specific gene for DNA and RNA of an infectious disease, a hereditary disease, drug tolerance, drug resistance, and a susceptible test sample, which includes the primer of the present invention as an active ingredient.

The primer according to the present invention may also include a base sequence in which one or more bases are deleted, substituted or added to the base sequence of each primer and a primer set.

The primer and primer set according to the present invention may include additional features that do not change the basic properties. That is, the base sequence can be modified using many means known in the art. Examples of such modifications may include methylation, capping, substitution of one or more homologs of a nucleotide, and modification of a nucleotide with an uncharged linkage such as phosphonate, phosphotriester, phosphoramidate, or carbamate, or charged linkage such as phosphorothioate or phosphorodithioate. Further, the nucleic acid may have one or more residues, which are additionally covalent-bonded, such as a protein such as a nuclease, a toxin, an antibody, a signal peptide, a poly-L-lysine, an intercalating agent such as acridine and psoralen, a chelating agent such as a metal, a radioactive metal, and an iron-oxidizing metal, and alkylation agent.

Further, the base sequence of the primer and primer set according to the present invention can be modified using a label capable of directly or indirectly providing a detectable signal. The primer and primer set may include a label that can be detected using spectroscopic, photochemical, biochemical, immunochemical, or chemical means. Useful labels include $^{32}P$, fluorescent dyes, electron dense reagents, enzymes (commonly used in ELISAS), biotin or hapten, and proteins that are available for antisera or monoclonal antibodies.

The primer and primer set according to the present invention can be chemically synthesized using any other well-known method including a phosphotriester method such as cloning and restriction enzyme digestion of appropriate sequences and Narang (1979, Meth, Enzymol. 68: 90-99), a diethylphosphoramidate method such as Beaucage (1981, Tetrahedron Lett. 22: 1859-1862), and the direct chemical synthesis methods such as the solid support methods of U.S. Pat. No. 4,458,066.

Hereinafter, the present invention will be described.

The present invention purposes to reduce the increased sensitivity and non-specifically occurring reaction due to an increase of amplification products in PCR by a complementary nucleotide sequence or a complementary nucleotide sequence including a mis-matched nucleotide sequence linked to 5'-terminal of the primer for PCR directly or through a linker.

The present invention relates to a PCR primer including a complementary nucleotide sequence or a complementary nucleotide sequence including a mis-matched nucleotide sequence linked to 5'-terminal of the primer directly or through a linker, and more specifically to a primer for PCR obtained by, directly or through inosine as a linker, linking a complementary nucleotide sequence or a complementary nucleotide sequence including a mis-matched nucleotide sequence to 5'-terminal of a forward or reverse primer, a PCR method including a step of mixing a nucleic acid template in a PCR composition including the primer and then performing PCR on the mixture. The PCR primer of the present invention includes a complementary nucleotide sequence or a complementary nucleotide sequence including a mis-matched nucleotide sequence so that there is the advantage that non-specific reaction occurred in the amplification reaction can be reduced.

Hereinafter, the present invention will be described.

The present invention provides a PCR primer in which a complementary nucleotide sequence or a complementary nucleotide sequence including a mis-matched nucleotide sequence is linked to 5'-terminal of a forward or reverse primer directly or through a linker.

In the present specification, the term "complementary nucleotide" refers to a nucleotide having a sequence complementary to the nucleotide sequence of the forward or reverse primer, and the direction of the corresponding nucleotide is located at the 5' terminal of the forward or reverse primer. A "mis-matched nucleotide sequence" included in a complementary nucleotide refers to a nucleotide sequence which is mis-matched with a forward or reverse primer nucleotide sequence. DNA base may be one of adenine, guanine, cytosine, thymine, and uridine. When the number of mis-matched nucleotides in the complementary primer is absent, the Tm value for the primer annealing becomes high, so that the annealing of the template DNA base sequence is not performed well, and thus the amplification reaction is not performed. Also, if the number of mis-matched nucleotides in the complementary primer exceeds 13, the Tm value of the primer will be significantly lowered, and the number of mis-matched nucleotides will be increased, resulting in a non-specific reaction during PCR execution. Therefore, the primer (CP) of the present invention generates bubbles according to the number of mis-matched nucleotides, and the melting Tm decreases as the number of mis-matched nucleotides increases. Accordingly, one to three bubbles are formed in the mis-matched nucleotide portion, the bubble portion, within the complementary sequence.

The linkage between a primer and the complementary primer may be directly connected, but a linker may also be used. In this case, the base used is inosine, and the number of the inosine base is preferably in the range of 1 to 9, though not particularly limited. In addition, the present invention provides a composition for PCR amplification including a DNA polymerase, dNTPs, a buffer solution for reaction, and the PCR primer.

As the reaction buffer solution, a conventional PCR buffer solution including components such as Tris-HCl, KCl, $(NH_4)_2SO_4$, and $MgCl_2$ can be suitably modified and used. The dNTPs refer to dATP, dTTP, dUTP, dGTP, and dCTP, and the DNA polymerase that can be used is not limited to a specific enzyme or a hot start effect. In a preferred embodiment of the present invention, Taq DNA polymerase (5'→3' exo +), Hot start Taq DNA polymerase (5'→3' exo +), Vent DNA polymerase (5'→3' exo –), and Pfu DNA polymerase (3'→5' exo +) are used to perform PCR. Further, the primer for PCR amplification can be used at a concentration ranging from 0.2 µM to 1 µM, and suitable primer concentrations can be easily determined by those skilled in the art.

The present invention relates to a PCR amplification method including mixing the nucleic acid template to PCR composition including a primer and then performing PCR on the mixture, in which the primer is used as a PCR primer including a complementary nucleotide sequence or a complementary nucleotide sequence linked a mis-matched nucleotide sequence in a complementary nucleotide sequence linked directly or via a linker to the 5'-terminal region of a primer to be amplified.

The PCR is carried out by repeating the denaturation, annealing, and extension steps, and this PCR principle is clear to the parties. The denaturation, annealing, and elongation, respectively, are preferably performed at 85° C. to 95° C. for 1 second to 60 seconds, at 40° C. to 70° C. for 1 second to 60 seconds, and at 50° C. to 75° C. for 1 second to 60 seconds, but it can be adjusted appropriately according to the reaction conditions. For example, according to a preferred embodiment of the present invention, when 2 to 3 mis-matched nucleotides are substituted in the primer, the melting temperature (hereinafter, referred to as "Tm") is lowered by about 5° C. to 10° C., when 4 to 6 mis-matched nucleotides are substituted in the primer, the melting temperature (hereinafter, referred to as "Tm") is lowered by about 10° C. to 20° C., and when 7 to 12 mis-matched nucleotides are substituted in the primer, the melting temperature (hereinafter, referred to as "Tm") is lowered by about 20° C. to 30° C. Such a temperature change of Tm may be somewhat changed depending on the kind of DNA polymerase used, the length of the primer, the kind of base in the primer, reaction conditions, and the like. Based on the degree of change in Tm as described above, it is possible to establish a primer production condition for imparting temperature equivalence when designing a primer including a mis-matched nucleotide in a complementary nucleotide sequence, and to introduce an appropriate number of mis-matched nucleotides, thereby increasing the specificity of the PCR.

Using the results of the following embodiments, it is possible to establish a primer production condition that gives temperature equivalence at the time of designing a primer for a primer position and to prepare a nucleotide sequence with a minimal difference in Tm values to be occurred by introducing a linker and a mis-matched nucleotide at a proper position in a complementary nucleotide sequence, thereby increasing the specificity of the PCR reaction. In addition, PCR specificity and sensitivity can be maintained with or without exonuclease (5'→3, 3'→5') function of the DNA polymerase used.

Advantageous Effects

As described above, by including the mis-matched nucleotide sequence or the complementary nucleotide sequence directly or via inosine linker linked to 5' position of a primer, amplification products are increased in the nucleic acid amplification reaction using DNA or RNA as a template, so that it is effective to improve sensitivity and to reduce the nonspecific reaction that occurs. These effects are all active regardless of the type of DNA polymerase.

DESCRIPTION OF DRAWINGS

FIGS. 4 and 5 illustrate the results according to a method of using the primer (CP) of the present invention as one of two primers necessary for nucleic acid amplification.

FIG. 7 illustrates a result of using Taq DNA polymerase,

FIG. 8 illustrates a result of using HotStart Taq DNA polymerase,

FIG. 9 illustrates a result of using Pfu DNA polymerase, and

FIG. 10 illustrates a result of using Vent DNA polymerase.

MODES OF THE INVENTION

Figure 1:
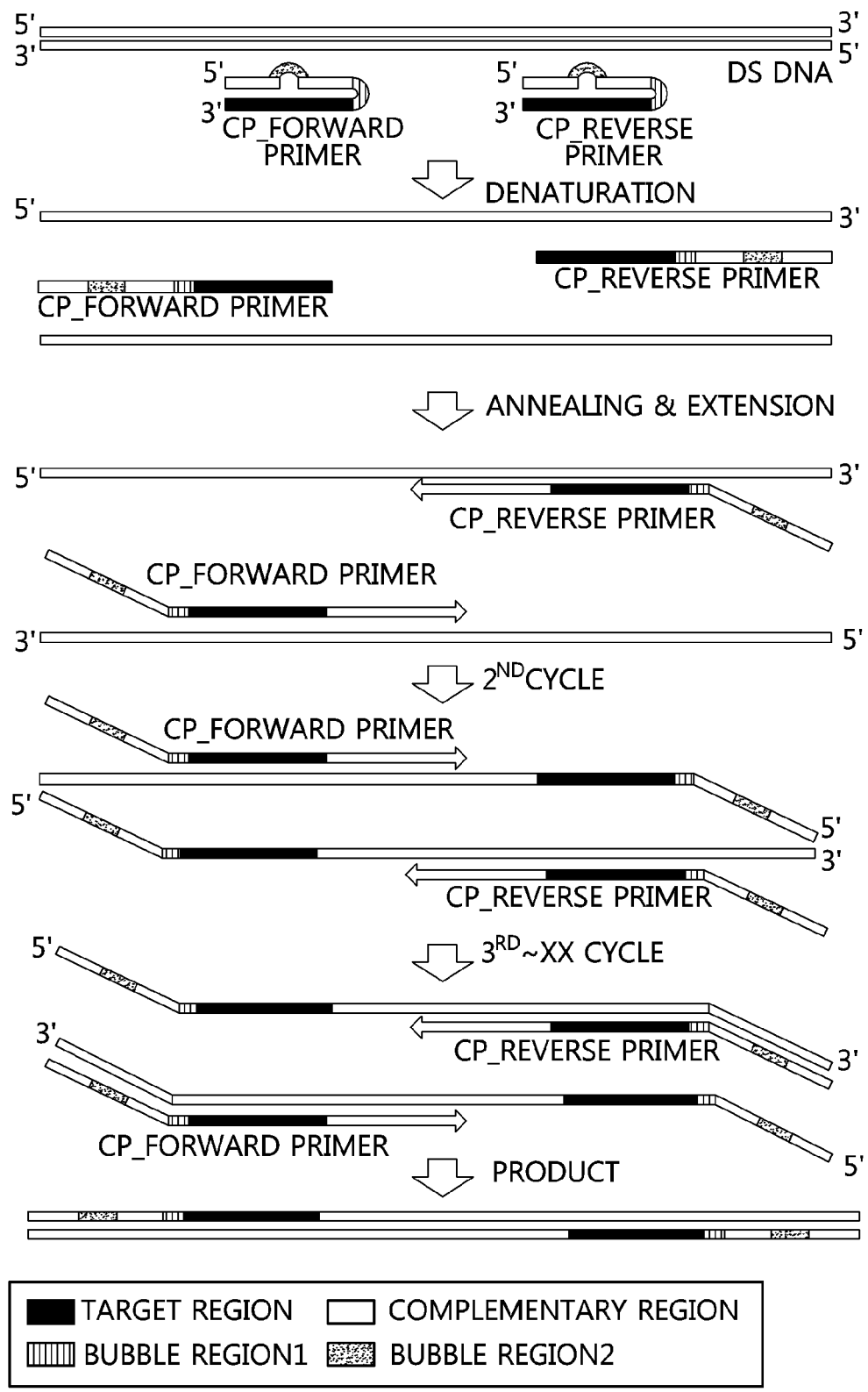
FIG. 1 is a sequential illustration of a method for amplifying double-stranded DNA using a primer (CP) of the present invention.
Figure 2:
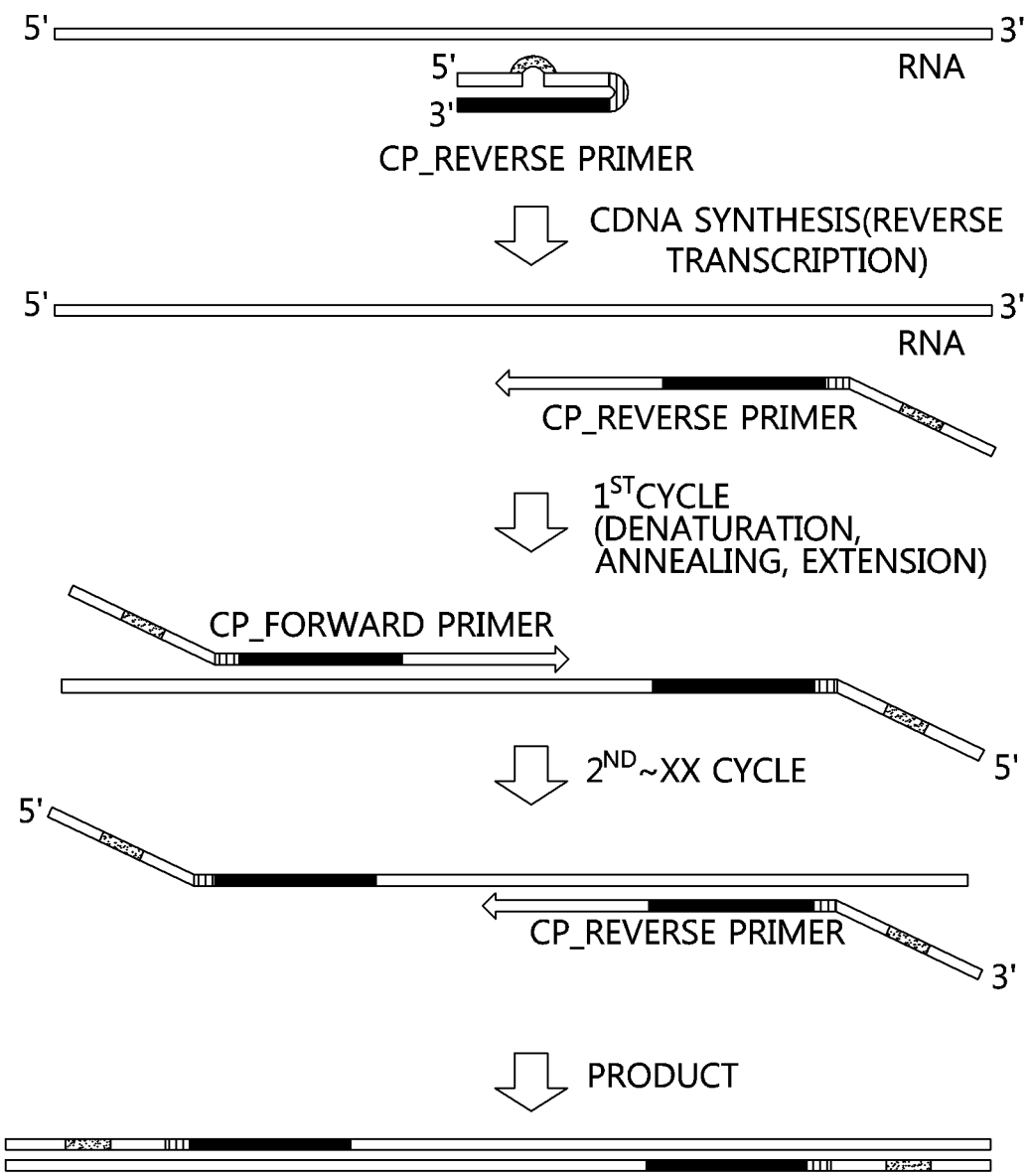
FIG. 2 is a sequential illustration of a method for amplifying single-stranded RNA using a primer (CP) of the present invention.

Hereinafter, the present invention will be described in more detail with reference to examples. However, the following examples are for illustrative purposes only and are not intended to limit the scope of the present invention.

Example 1: Analysis of Effects of the Linker of the Bubble Portion 1 of the Primer (CP) of the Present Invention DNA template for HIV tat amplification was prepared in which HIV tat plasmid DNA was prepared by a gene synthesis of HIV-1 isolate 10BR_PE064 (GI: 672918720, 5281-5700 bp) to plasmid DNA.

In the primer (CP) of the present invention, the forward primer and reverse primer for the HIV tat gene of the conventional method (Nucleic Acids Research, 36:20, 2008) were designed as target regions, the complementary sequence thereto was positioned at the 5'-terminal thereof, and the complementary sequence included 7 to 8 mis-matched sequences. The inosine linker was designed as SEQ ID NOS: 3 to 10 at the bubble portion 1 between the target region and the complementary sequence. SEQ ID NO: 3 was a primer including no linker in the bubble portion 1, and SEQ ID NOS: 4 to 10, respectively, were designed to include 1 (Ix1a, Ix1b, Ix1c), 3 (Ix3), 5 (Ix5), 7 (Ix7), and 9 (Ix9) inosine linkers.

The control group was used a mixture in which SEQ ID NO 1 was used as a forward primer and SEQ ID NO 2 was used as a reverse primer in the prepared primer. The experimental group was prepared in a mixture in which the primers (CP) of the present invention of SEQ ID NOS: 3 to 10 were used as a forward primer and SEQ ID NO 2 was used as a reverse primer.

The mixture for the nucleic acid amplification reaction using the primers was prepared in a reaction mixture including 3.0 mM MgCl$_2$, 0.2 mM dNTPs (NEB), 1.75 U Taq DNA polymerase, 10 ng Human genomic DNA, and 0.5 M primer set. The nucleic acid amplification reaction was performed in that 45 ul of the reaction mixture and 5 ul of the template DNA in 69, 6.9 and 0.69 fg/ul, respectively, were added, and the initial denaturation step at 94° C. for 10 minutes, the denaturation step at 94° C. for 30 seconds, the annealing step at 55° C. for 30 seconds, and the extension step at 72° C. for 2 minutes were carried out for 40 cycles and the final extension step were carried out at 72° C. for 7 minutes. 5 ul of the amplification product was subjected to electrophoresis analysis on 2% agarose gel including gel green dye.

Figure 3:
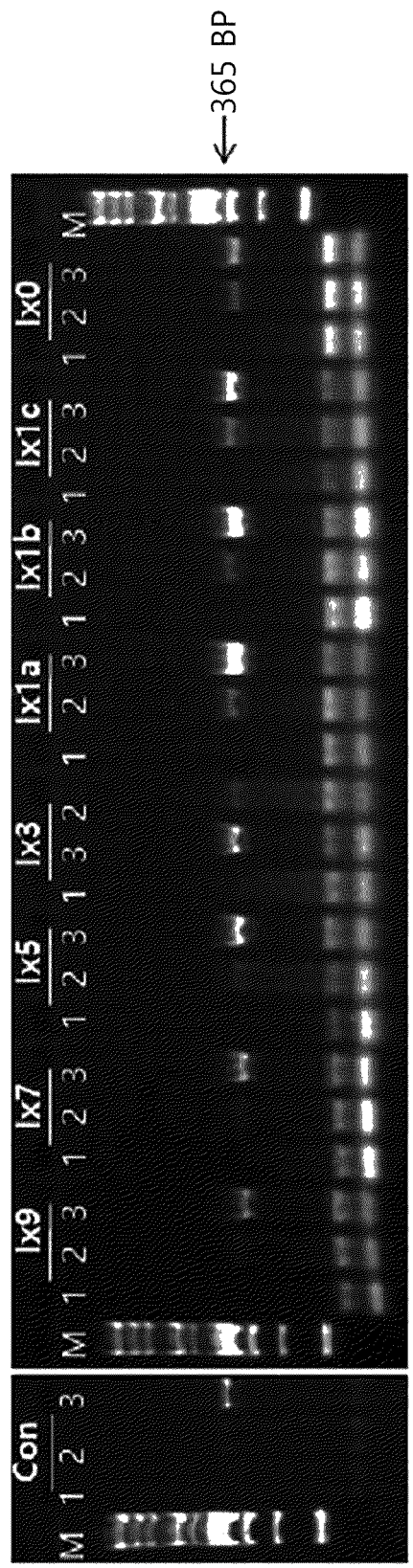
FIG. 3 illustrates a result according to the number of deoxyinosine included in a bubble portion 1 located at 5'-terminal of a target region of a primer (CP) of the present invention in a method of using the primer (CP) of the present invention as one of two primers necessary for nucleic acid amplification.

As a result, as illustrated in FIG. 3, it was exhibited that amplification products of the primers (CP) of the present invention (lines 3 of Ix9, Ix7, Ix5, Ix3, Ix1a, Ix1b, Ix1c, and Ix0) increased as compared with the conventional primer (line 3 of Con) in lines 3 in which the templates reacted in a concentration of 345 fg. It was exhibited that amplification products of the primers (CP) of the present invention (lines 2 of Ix7, Ix5, Ix3, Ix1a, Ix1b, Ix1c, and Ix0) increased as compared with the conventional primer (line 2 of Con) in lines 2 in which the template concentration was 34 fg. As a result of the above reaction, Ix1, Ix3, Ix5 and Ix7 of the primer (CP) of the present invention were confirmed to exhibit an increase in amplification product compared to Ix0. Accordingly, the amplification product of the nucleic acid amplification reaction was confirmed to increase as the inosine was included in the bubble portion 1 of the primer (CP) of the present invention.

Example 2: Analysis of Effects According to the Number of Mis-Matched Sequences on a Bubble Portion 2 of the Primer (CP) of the Present Invention HIV tat plasmid DNA was used as a template. The primer (CP) of the present invention included one inosine on the bubble portion 1, and then 0, 3, 8, and 12 numbers of mis-matched sequences were included on the bubble portion 2, thereby preparing SEQ ID NOS: 11, 12, 4, and 13.

The control group was used a mixture in which SEQ ID NO: 1 was used as a forward primer and SEQ ID NO: 2 was used as a reverse primer in the prepared primer. The experimental group was prepared in a mixture in which the primers (CP) of the present invention of SEQ ID NOS: 11, 12, 4, and 13 were used as a forward primer and SEQ ID NO: 2 was used as a reverse primer.

The mixture for the nucleic acid amplification reaction using the primers was prepared in a reaction mixture including 3.0 mM MgCl$_2$, 0.2 mM dNTPs, 1.75 U Taq DNA polymerase, 10 ng Human genomic DNA, and 0.5 μM primer set. The nucleic acid amplification reaction was performed in that 45 ul of the mixture and 5 ul of the template DNA in 69, 6.9 and 0.69 fg/ul, respectively, were added, and the initial denaturation step at 94° C. for 10 minutes, the denaturation step at 94° C. for 30 seconds, the annealing step at 55° C. for 30 seconds, and the extension step at 72° C. for 2 minutes were carried out for 40 cycles and the final extension step were carried out at 72° C. for 7 minutes. 5 ul of the amplification product was subjected to electrophoresis analysis on 2% agarose gel including gel green dye.

Figure 4:
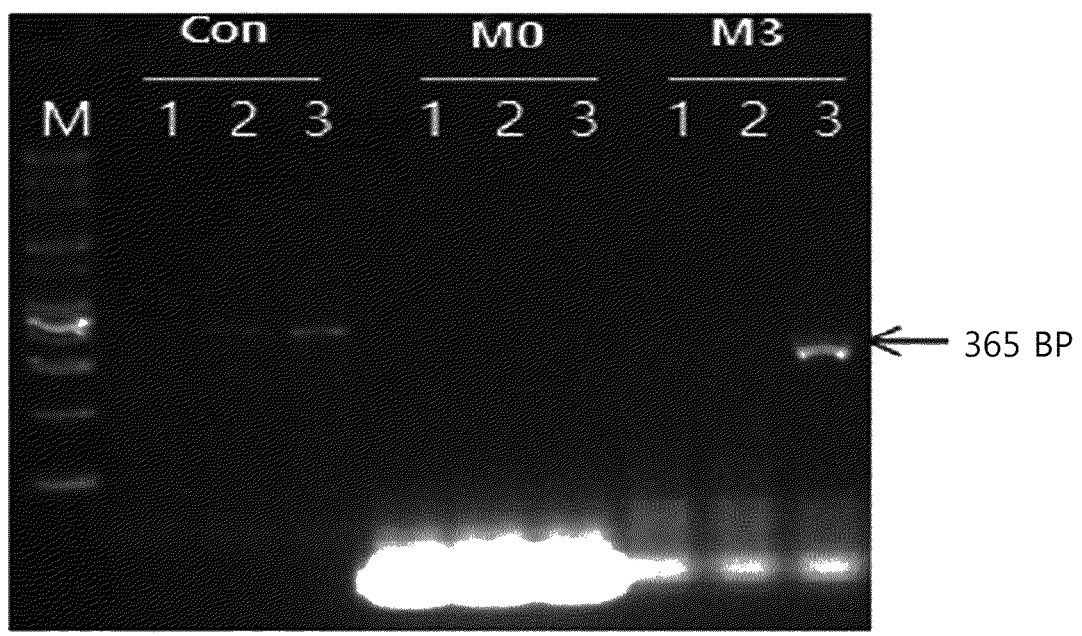
FIGS. 4 and 5 illustrate a result according to the number of mis-matched nucleotides (0, 3, 7, and 12) in a bubble portion 2 located at a complementary portion of a primer (CP) of the present invention.

M0 illustrated in FIG. 4 was the result of using SEQ ID NO: 11 without the mis-matched sequence as a forward primer and no amplification product was generated. M3 was SEQ ID NO: 12 including 3 mis-matched sequences, and the amplification product of line 3 of M3 increased than that of line 3 of Con in lines 3 where 345 fg of template DNA reacted in the conventional primer (SEQ ID NO: 1). However, in the lines 2 in which 34.5 fg reacted, the amplification product was not detected in line 2 of M3.

Figure 5:
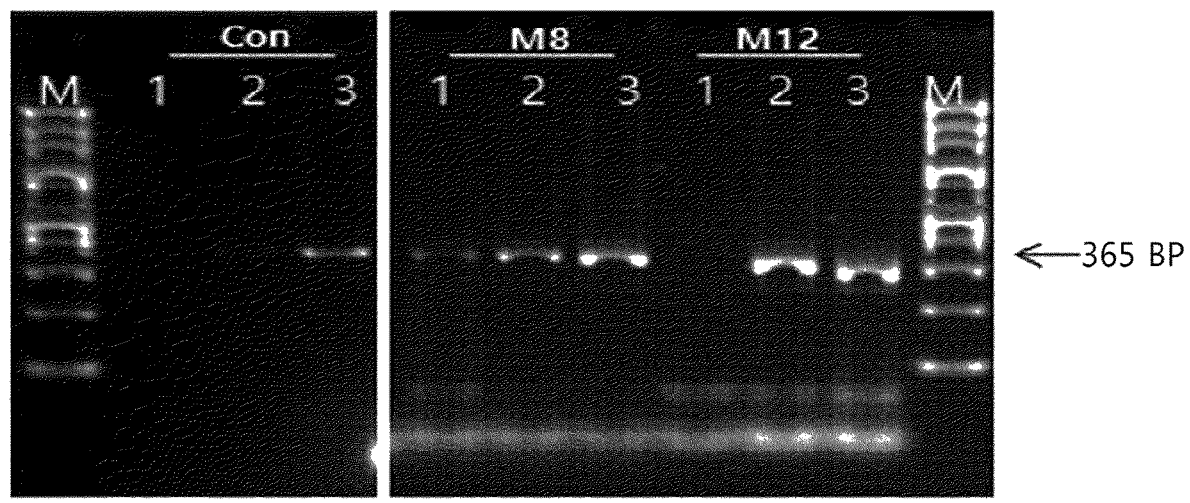

M8 illustrated in FIG. 5 was SEQ ID NO: 4 including 8 mis-matched sequences, and M12 was SEQ ID NO: 13 including 12 mis-matched sequences. Their amplification products were confirmed to be detected in the lines 1 in which the template DNA reacted in 3.45 fg than the conventional primer (SEQ ID NO: 1). In particular, the amplification product in M8 was confirmed to be the most increased. As a result, increase and sensitivity enhancement of the amplification product were confirmed to be depending on the number of mis-matched sequences on the bubble portion 2 of the primer (CP) of the present invention.

Example 3: Analysis of Effects According to the Number of Bubbles of the Primer (CP) of the Present Invention The primer (CP) of the present invention includes inosine on a bubble portion 1 and mis-matched sequence on a bubble portion 2. The bubble portion 1 formed one bubble, and the bubble portion 2 formed three bubbles.

SEQ ID NO: 13 produced totally two bubbles, one on the bubble portion 1 and one on the bubble portion 2. SEQ ID NO: 14 produced one bubble on the bubble portion 1 and two bubbles on the bubble portion 2. SEQ ID NO: 15 produced one bubble on the bubble portion 1 and three bubbles on the bubble portion 2. Using the primer (CP) of the present invention as a forward primer and using SEQ ID NO: 2 as a reverse primer, the mixture for the nucleic acid amplification reaction was prepared in a reaction mixture including 3.0 mM $MgCl_2$, 0.2 mM dNTPs, 1.75 U Taq DNA polymerase, 10 ng Human genomic DNA, and 0.5 µM primer set.

The nucleic acid amplification reaction was performed in that 45 ul of the reaction mixture and 5 ul of the template DNA in 69, 6.9 and 0.69 fg/ul, respectively, were added, and the initial denaturation step at 94° C. for 10 minutes, the denaturation step at 94° C. for 30 seconds, the annealing step at 45° C. for 30 seconds, and the extension step at 72° C. for 2 minutes were carried out for 40 cycles and the final extension step were carried out at 72° C. for 7 minutes. 5 ul of the amplification product was subjected to electrophoresis analysis on 2% agarose gel including gel green dye.

Figure 6:
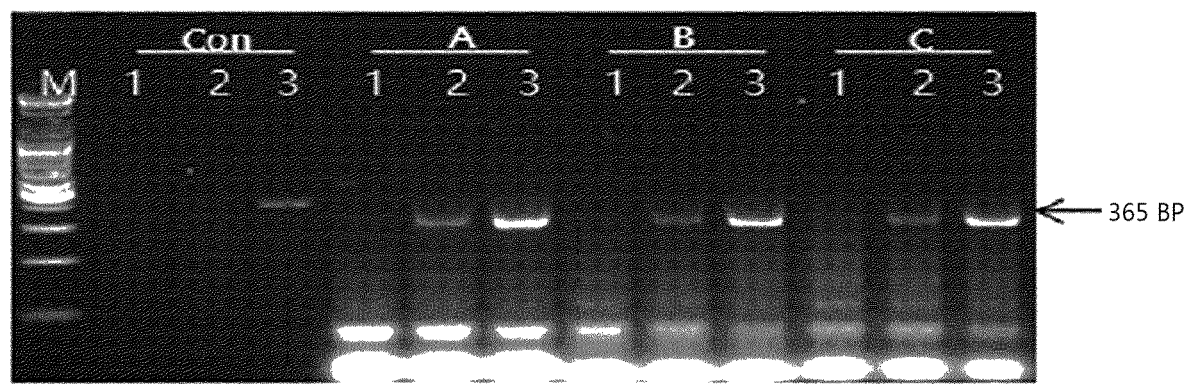
FIG. 6 illustrates a result using a primer (CP) of the present invention in which the number of total bubbles is 2, 3, and 4, respectively by including a bubble portion 1 and bubble portion 2 of a primer (CP) of the present invention in a method of using the primer (CP) of the present invention as one of two primers necessary for nucleic acid amplification.

As a result of using the primer (CP) of the present invention in which the number of bubbles is 2 in each A line, the number of bubbles is 3 in each B line, and the number of bubbles is 4 in each C line as illustrated in FIG. 6, the amplification reaction was detected in the lines 2 in which the template DNA was up to 34.5 fg, in which the number of bubbles was 2 to 4, and the amplification product was confirmed to increase than the line 3 of Con in the lines 3 using 345 fg.

Example 4: Analysis of the Amplification Reaction of the Primer (CP) of the Present Invention by Type of DNA Polymerase In order to confirm the amplification reaction of the primer (CP) of the present invention according to the DNA polymerase used in the nucleic acid amplification reaction, the primer (CP) of the present invention of SEQ ID NO: 4 was used as a forward primer, and SEQ ID NO: 2 was used as a reverse primer. The amplification reaction was analyzed by Taq DNA polymerase, HotStart Taq DNA polymerase, Vent DNA polymerase, and Pfu DNA polymerase.

Figure 7:
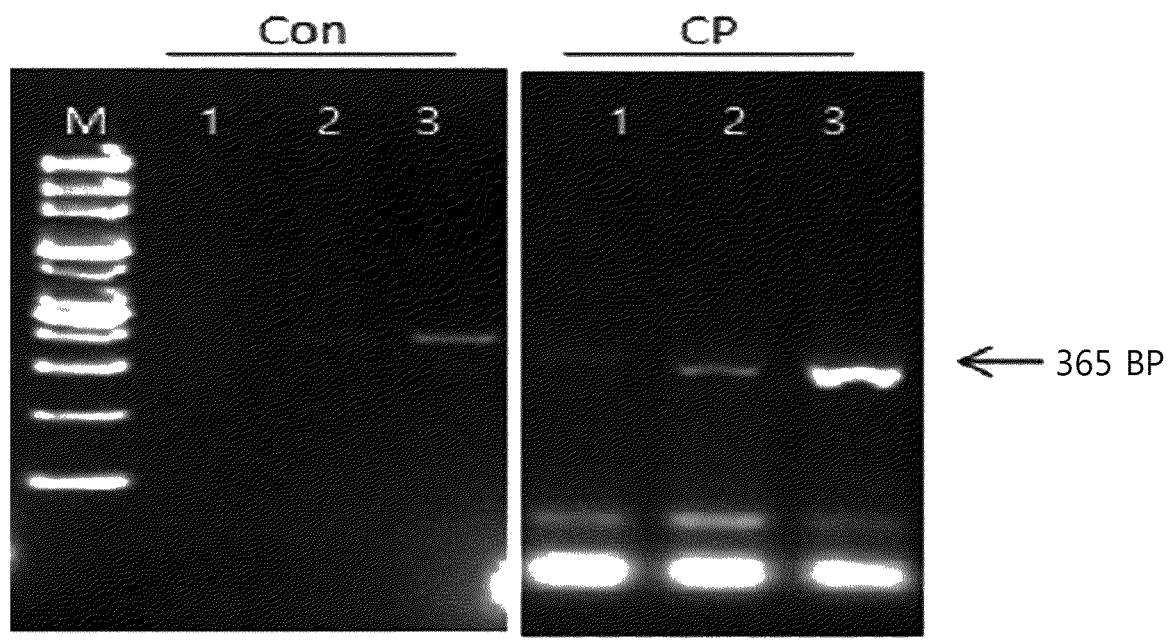
FIGS. 7 to 10 illustrate a method of using the primer (CP) of the present invention as one of two primers necessary for nucleic acid amplification.

In the nucleic acid amplification reaction as illustrated in FIG. 7, the mixture for the nucleic acid amplification reaction of the Taq DNA polymerase was prepared in a reaction mixture including 3.0 mM $MgCl_2$, 0.2 mM dNTPs, 1.75 U Taq DNA polymerase, 10 ng Human genomic DNA, and 0.5 µM primer set.

Figure 8:
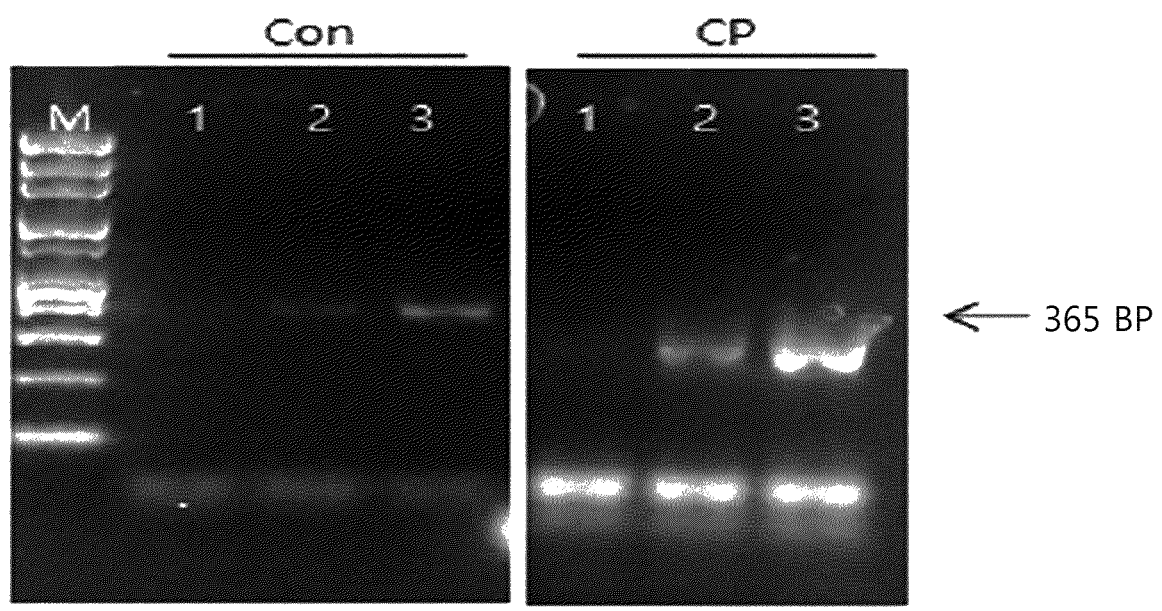

In the nucleic acid amplification reaction as illustrated in FIG. 8, the mixture for the nucleic acid amplification reaction of the HotStart Taq DNA polymerase was prepared in a reaction mixture including 3.0 mM $MgCl_2$, 0.2 mM dNTPs, 1.75 U HotStart Taq DNA polymerase, 10 ng Human genomic DNA and 0.5 µM primer set.

Figure 9:
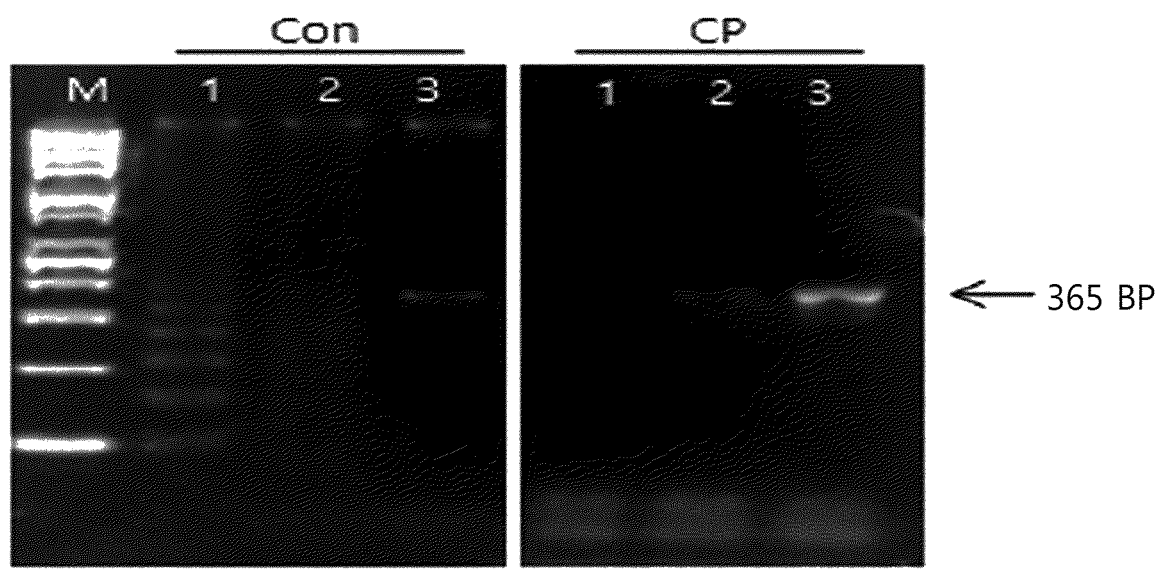

In the nucleic acid amplification reaction as illustrated in FIG. 9, the mixture for the nucleic acid amplification reaction of the Pfu DNA polymerase was prepared in a reaction mixture including 2.0 mM $MgSO_4$, 0.2 mM dNTPs, 1.75 U Pfu DNA polymerase, 10 ng Human genomic DNA and 0.5 µM primer set.

Figure 10:
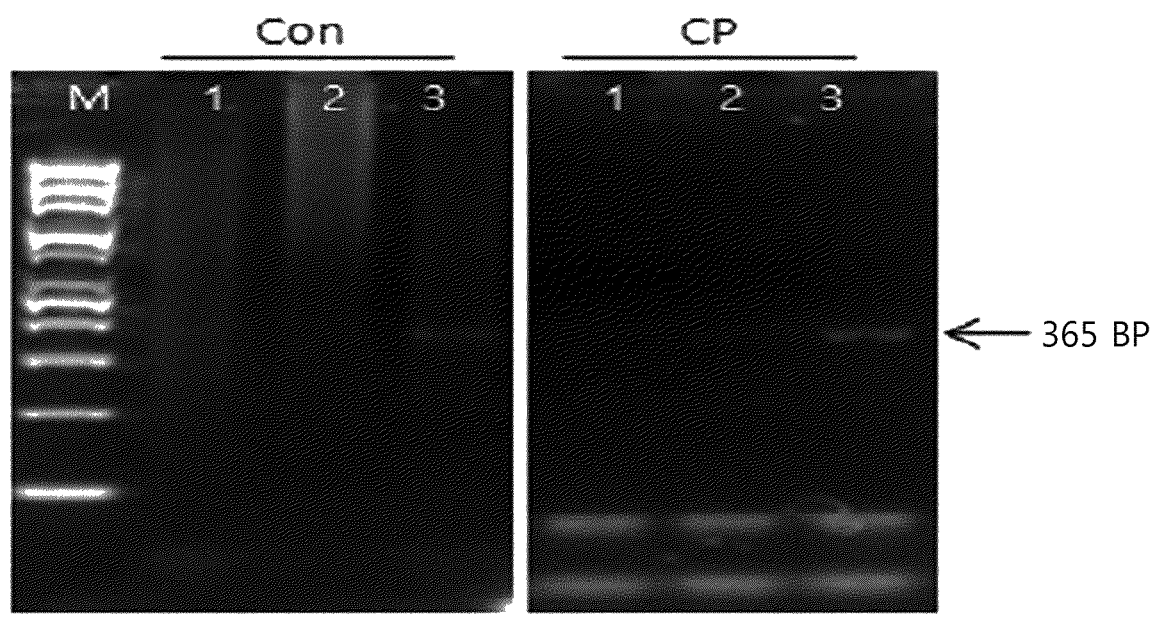

In the nucleic acid amplification reaction as illustrated in FIG. 10, the mixture for the nucleic acid amplification reaction of the Vent DNA polymerase was prepared in a reaction mixture including 1× buffer (20 mM Tris-HCl, 10 mM $(NH_4)_2SO_4$, 10 mM KCl, 2 mM $MgSO_4$, 0.01% TritonX-100, pH 8.8), 0.2 mM dNTPs, 1.75 U Vent DNA polymerase, 10 ng Human genomic DNA, and 0.5 µM primer set.

The nucleic acid amplification reaction was performed in that 45 ul of the reaction mixture and 5 ul of the template DNA in 69, 6.9 and 0.69 fg/ul, respectively, were added, and the initial denaturation step at 94° C. for 10 minutes, the denaturation step at 94° C. for 30 seconds, the annealing step at 45° C. for 30 seconds, and the extension step at 72° C. for 2 minutes were carried out for 40 cycles and the final extension step were carried out at 72° C. for 7 minutes. 5 ul of the amplification product was subjected to electrophoresis analysis on 2% agarose gel including gel green dye.

As a result of the Taq DNA polymerase as illustrated in FIG. 7, the amplification product was not confirmed in line 1 of Con using template DNA 3.45 fg, but the amplification product was confirmed in line 1 of the primer (CP) of the present invention.

As a result of the Hotstart Taq DNA polymerase as illustrated in FIG. 8, the amplified product in line 2 of the primer (CP) of the present invention was confirmed to increase as compared to that in line 2 of Con using template DNA 34.5 fg.

As a result of the Pfu DNA polymerase as illustrated in FIG. 9, the amplification product was not confirmed in line 2 of Con using template DNA 34.5 fg, but the amplification product was confirmed in line 2 of the primer (CP) of the present invention. In line 1 of Con using template DNA 3.45 fg, many amplified products of 100 bp or more were detected. However, in line 1 of the primer (CP) of the present invention, an amplification product of 100 bp or more could not be confirmed.

As a result of the Vent DNA polymerase as illustrated in FIG. 10, exhibited that the amplification products of line 3 of Con using the template DNA 345 fg and the line 3 of the primer (CP) of the present invention exhibited similar band thicknesses, but all of the lines 1, 2, and 3 exhibited a drag phenomenon, and the lines 1, 2 and 3 of the primer (CP) of the present invention exhibited no drag phenomenon.

Example 5: Analysis of Amplification Reaction According to the Application of Each or Pair of the Forward and Reverse Primers of the Primer (CP) of the Present Invention As illustrated in FIG. 11, the nucleic acid amplification reaction was carried out in which and SEQ ID NO: 16 was a forward primer and SEQ ID NO: 17 was a reverse primer in Con line, a primer of the conventional method (Nucleic Acids Research, 36:20, 2008) for amplification of the beta actin gene of human genomic DNA.

The primer (CP) of the present invention includes one inosine in the bubble portion 1 and four mis-matched sequences in the bubble portion 2 to produce the primer (CP) of the present invention having SEQ ID NO: 18 and SEQ ID NO: 19 for SEQ ID NO: 16 and SEQ ID NO: 17.

Figure 11:
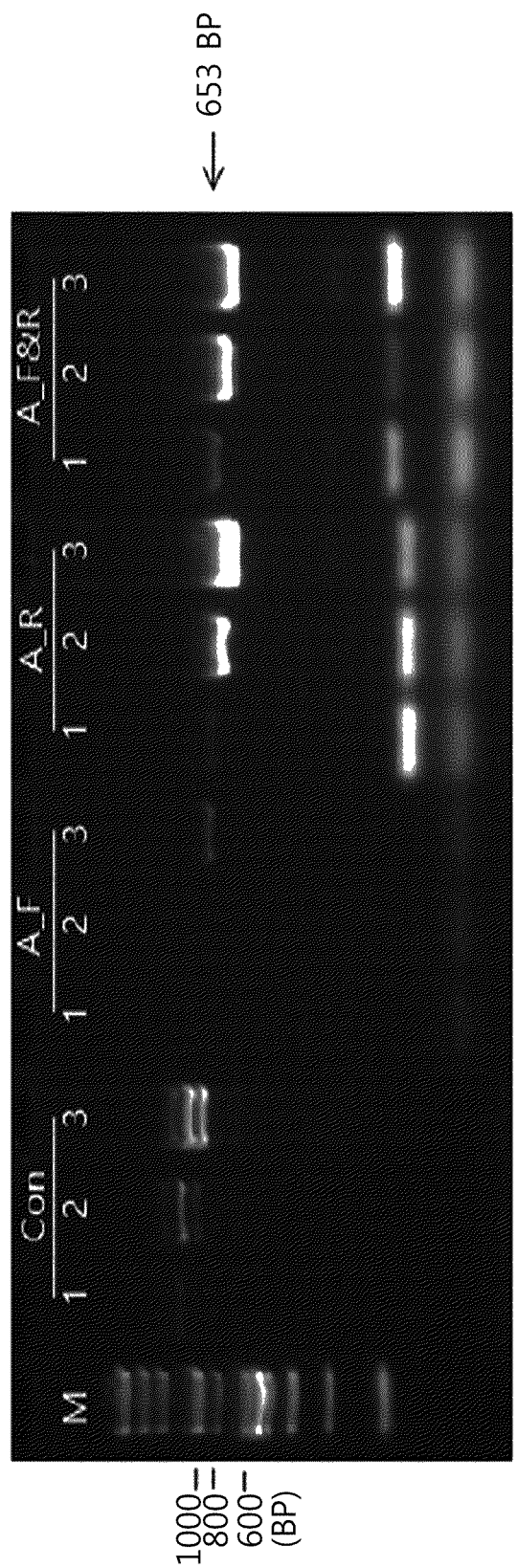
FIG. 11 illustrates a result of a reaction, as a forward primer and a reverse primer, using each of two primers necessary for nucleic acid amplification of a beta-actin gene in human gDNA as a primer (CP) of the present invention and a result of an amplification reaction using all two primers necessary for nucleic acid amplification of a beta-actin gene in human gDNA as a primer (CP) of the present invention.

Using the primer (CP) of the present invention, the nucleic acid amplification reaction was carried out in which SEQ ID NO: 18 of the primer (CP) of the present invention was used as a forward primer and a conventional SEQ ID NO: 17 primer was used as a reverse primer in A_F line as illustrated in FIG. 11, and the nucleic acid amplification reaction was carried out in which SEQ ID NO: 16 of the conventional primer, was used as a forward primer, and SEQ ID NO: 19 of the primer (CP) of the present invention, was used as a reverse primer in A_R line. In A_F&R line, SEQ ID NO: 18 and SEQ ID NO: 19 of the primer (CP) of the present invention, were used as a forward and reverse primers, respectively.

The mixture of the nucleic acid amplification reaction for the primer set was prepared in a reaction mixture including 2.5 mM $MgCl_2$, 0.2 mM dNTPs, 1.25 U Taq DNA polymerase, and 0.5 µM primer set.

The reaction mixture and 100, 10, and 1 ng, respectively, of human genomic DNA (Promega, G3041) were added and then total 50 ul of reaction product was subject to the nucleic acid amplification reaction in which the initial denaturation step at 94° C. for 2 minutes, the denaturation step at 94° C. for 30 seconds, the annealing step at 60° C. for 30 seconds, and the extension step at 72° C. for 45 seconds were carried out for 40 cycles and the final extension step were carried out at 72° C. for 7 minutes. 5 ul of the amplification product was subjected to electrophoresis analysis on 2% agarose gel including gel green dye.

As a result according to the nucleic acid amplification reaction, a single-band amplification products of the A_F, A_R, and A_F & R lines using the primer (CP) of the present invention were exhibited, and there or more bands, as the amplification products, in the Con line using the conventional primer were exhibited. The amplification product for the beta actin gene was a single amplification product corresponding to 653 bp, and the result according to the primer (CP) of the present invention of FIG. 11 is confirmed to be higher than specificity of the conventional primer. The specificity of the primer (CP) of the present invention was confirmed to increase even when only one of the forward and reverse primers was applied. The increasing effect of the amplification product was confirmed when the primer (CP) of the present invention was applied to only one of the two primers, and the increase of the amplification product was also confirmed when using a pair of primers.

Figure 12:
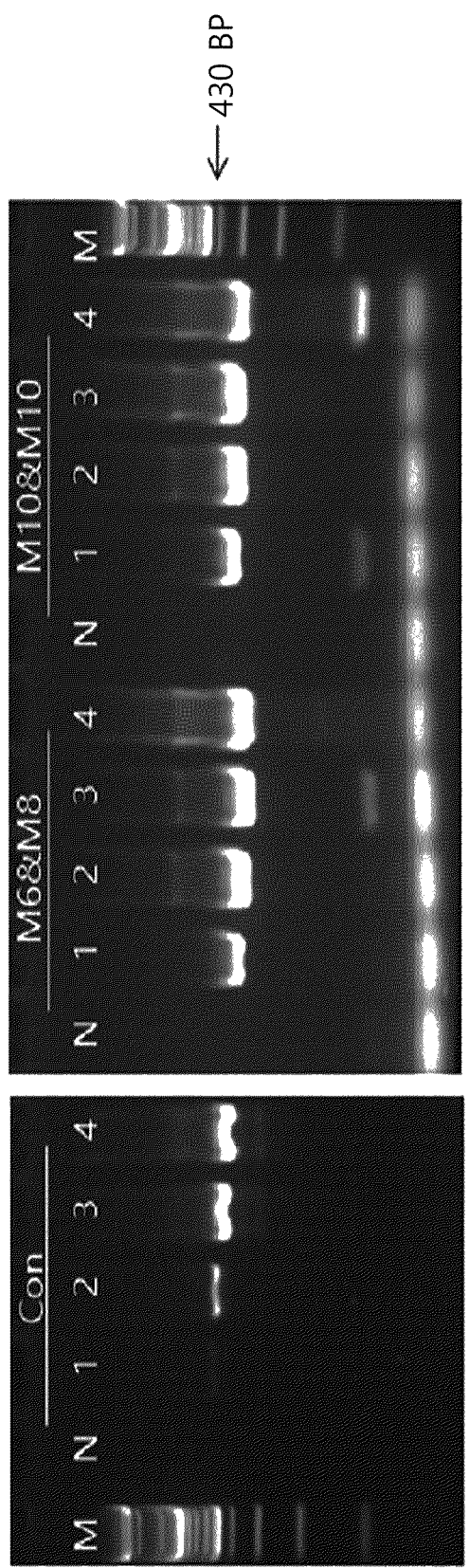
FIG. 12 illustrates a result of an amplification reaction using the primer (CP) of the present invention as two primers necessary for nucleic acid amplification of GAPD gene in Rat gDNA.

As illustrated in FIG. 12, for amplifying the GAPD gene of Rat genomic DNA, SEQ ID NO: 20 of (Nucleic Acids Research, 36:20, 2008) CP was used as a forward primer, and SEQ ID NO: 21 was used as a reverse primer. SEQ ID NO: 22 of 6 mis-matched sequences in the bubble portion 2 and SEQ ID NO: 24 of 10 mis-matched sequences in the bubble portion 2 were used as a forward primer, and SEQ ID NO: 23 of 8 mis-matched sequences and SEQ ID NO: 25 of 10 mis-matched sequences were used as a reverse primer in the primer (CP) of the present invention The mixture of the nucleic acid amplification reaction for the primer set was prepared in a reaction mixture including 2.0 mM $MgCl_2$, 0.2 mM dNTPs, 1 U Taq DNA polymerase, and 0.5 µM primer set.

The reaction mixture and 1000, 100, 10, and 1 pg, respectively, of Rat genomic DNA (Clonetech, Cat. No. 636404) were added and then total 25 ul of reaction product was subject to the nucleic acid amplification reaction in which the initial denaturation step at 94° C. for 5 minutes, the denaturation step at 94° C. for 30 seconds, the annealing step at 55° C. for 30 seconds, and the extension step at 72° C. for 30 seconds were carried out for 35 cycles and the final extension step were carried out at 72° C. for 7 minutes. 5 ul of the amplification product was subjected to electrophoresis analysis on 2% agarose gel including gel green dye.

The line 1 illustrated in FIG. 12 is the amplification product of the nucleic acid amplification reaction using 1 pg of Rat genomic DNA. It was confirmed that the amplification products of the lines 1 of M6 and M8 for SEQ ID NO: 22 and SEQ ID NO: 23, respectively, in which 6 and 8 mis-matched sequences were applied to the bubble portion 2 of the primer (CP) of the present invention and the lines 1 of M10 and M10 for SEQ ID NO: 24 and SEQ ID NO: 25, respectively, in which 10 and 10 mis-matched sequences were applied to the bubble portion 2 of the primer (CP) of the present invention increased to compared with the line 1 of Con. As a result of the above-mentioned 11 and 12, it was confirmed that when the primer (CP) of the present invention applied to only one or two pairs among the pairs of primer for the nucleic acid amplification reaction results in an increase of the specificity and the amplification product. The increase in the amplification product was also confirmed in the combination of two pairs of primers (CP) of the present invention having different mis-matched sequence numbers of the primer (CP) of the present invention.

Example 6: Verification of Amplification Efficiency of RT-PCR Using the Primer (CP) of the Present Invention RT-PCR was performed using a conventional primer (Nucleic Acids Research, 36:20, 2008) and the primer (CP) of the present invention to amplify the beta actin gene in human total RNA (Stratagene, Cat. No. 750500). In order to synthesize RNA into cDNA as the first step of RT-PCR, SEQ ID NO: 17 corresponding to the reverse primer of the conventional primer set was used, and, cDNA was synthesized using SEQ ID NO: 19 with 4 mis-matched sequences, SEQ ID NO: 27 with 6 mis-matched sequences, and SEQ ID NO: 29 with 8 mis-matched sequences, respectively, in the bubble portion 2 of the primer (CP) of the present invention.

For cDNA synthesis, a mixture was prepared to include 1× buffer (50 mM Tris-HCl, pH 8.3, 3 mM $MgCl_2$, 10 mM DTT, 75 mM KCl), 2 mM dNTPs, 1 M primer, 200 U M-MLV RTase, and Human total RNA 40, 4, 0.4 ng.

The mixture for cDNA synthesis reaction reacted at 45° C., 55° C., and 65° C., respectively, for 60 minutes, and then the M-MLV RTase was inactivated at 94° C. for 5 minutes. The nucleic acid amplification reaction was carried out, in which the cDNA reaction solution was used as a template, and SEQ ID NO: 16 and SEQ ID NO: 17 were used as a primer set for the reaction solution synthesized in SEQ ID NO: 17, SEQ ID NO: 18 and SEQ ID NO: 19 were used as a primer set for the reaction solution synthesized in SEQ ID NO: 19, SEQ ID NO: 26 and SEQ ID NO: 27 were used as a primer set for the reaction solution synthesized in SEQ ID NO: 27, and SEQ ID NO: 28 and SEQ ID NO: 29 were used as a primer set for the reaction solution synthesized in SEQ ID NO: 29, respectively.

The mixture of the nucleic acid amplification reaction for the primer set was prepared in a reaction mixture including 2.5 mM $MgCl_2$, 0.2 mM dNTPs, 1.25 U Taq DNA polymerase, and 0.5 M primer set.

The reaction mixture and each 5 ul of cDNA reaction solution (2, 0.2, and 0.02 ng) of each primer for Human total RNA were added and then total 50 ul of the reaction product was subject to the nucleic acid amplification reaction in which the initial denaturation step at 94° C. for 2 minutes, the denaturation step at 94° C. for 30 seconds, the annealing step at 60° C. for 30 seconds, and the extension step at 72° C. for 45 seconds were carried out for 40 cycles and the final extension step were carried out at 72° C. for 7 minutes. 5 ul of the amplification product was subjected to electrophoresis analysis on 2% agarose gel including gel green dye.

Figure 13:
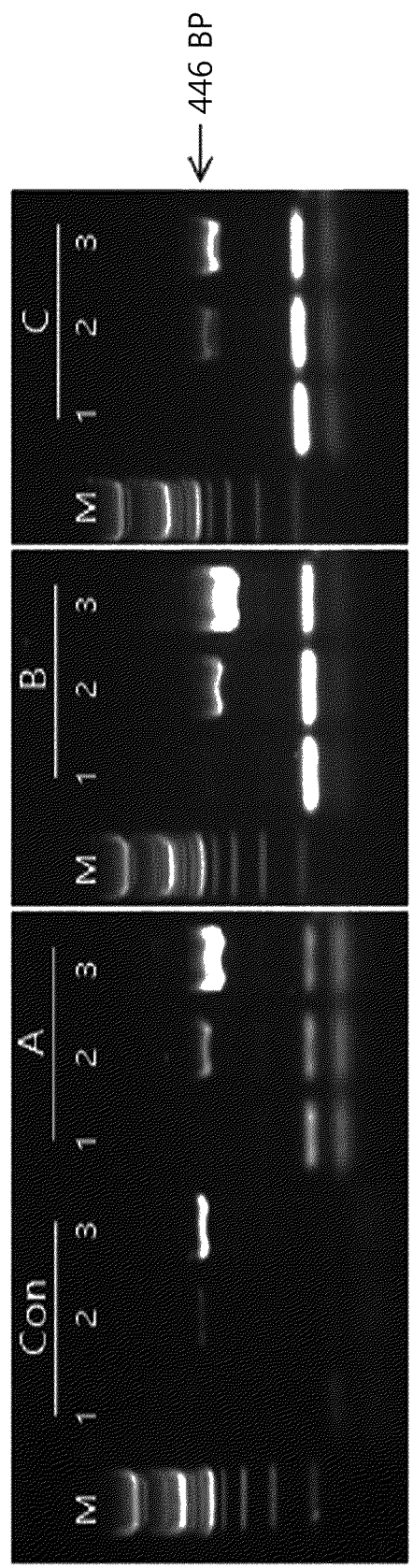
FIGS. 13 to 15 illustrate RT-PCR results depending on the cDNA synthesis temperature according to the number of mis-matched nucleotides in a bubble portion 2 located at a complementary region of a primer (CP) of the present invention.
Figure 14:
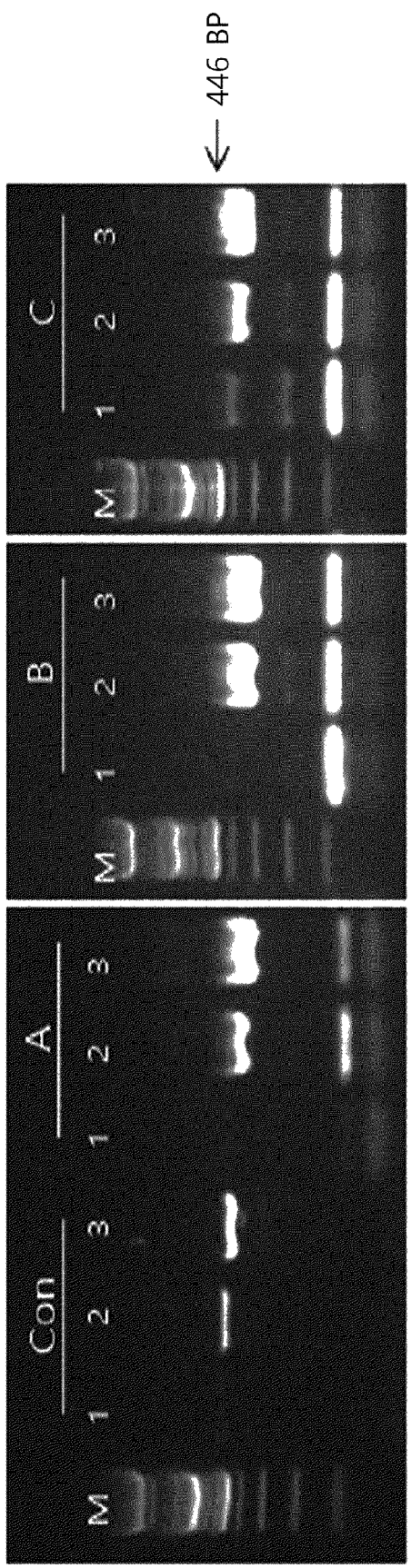
Figure 15:
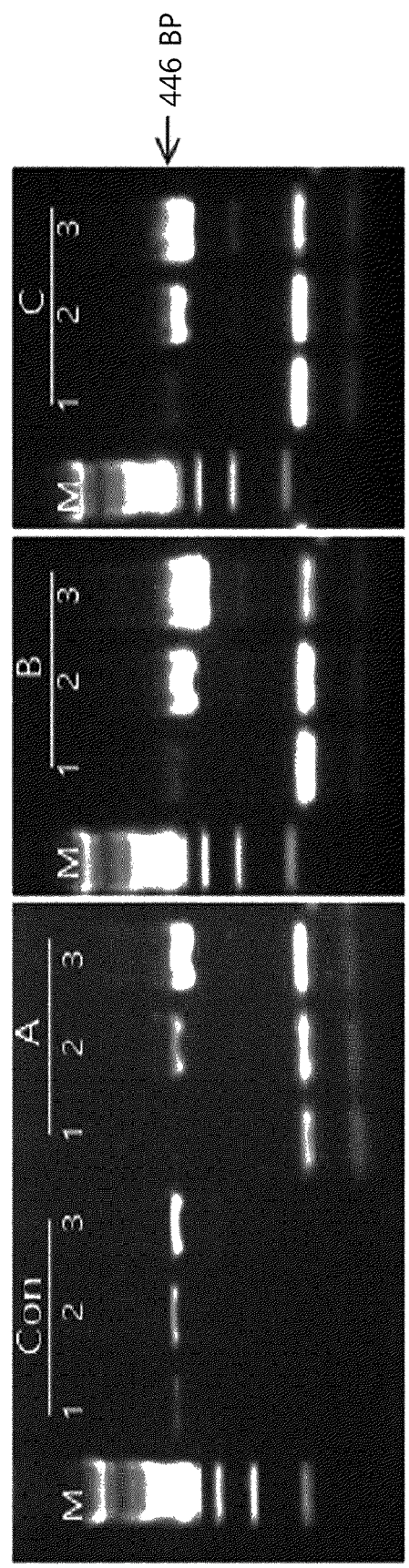

FIG. 13 illustrates the result of carrying out the cDNA synthesis reaction at 65° C., and the amplification products of A, B, and C lines, respectively, including 4, 6, and 8 mis-matched sequences in the bubble portion 2 of the primer (CP) of the present invention were confirmed to increase compared to the conventional primer Con line. FIG. 14 illustrates the result of carrying out the cDNA synthesis reaction at 55° C., and the amplification products of the primer (CP) of the present invention was confirmed to increase compared to that of the conventional primer, and that the amplification product of line 1 of C including 8 mis-matched sequences increased compared to those of the lines 1 of Con, A, and B. FIG. 15 illustrates the result of carrying out the cDNA synthesis reaction at 45° C., and the amplification products of the primer (CP) of the present invention was confirmed to increase compared to that of the conventional primer, and that the amplification products of the line 1 of C including 6 and 8 mis-matched sequences increased compared to those of the lines 1 of Con and A. As a result, the reactivity of the primer (CP) of the present invention was confirmed to increase as compared with the conventional primer set according to the temperature range during cDNA synthesis. Therefore, the primer (CP) of the present invention was used to confirm the usefulness of an amplification reaction of a specific gene by RT-PCR in single-stranded RNA.

What is claimed is:

1. A primer for gene amplification, wherein the primer is selected from the group consisting of SEQ ID NOs: 4 to 15.

2. A kit comprising the primer of claim 1.

* * * * *